United States Patent [19]

Defares et al.

[11] 4,064,869

[45] Dec. 27, 1977

[54] APPARATUS FOR REGULATING THE BREATHING PATTERN

[76] Inventors: Peter Bernard Defares, Emmalaan 9, Driebergen; Wouter Wies van der Schaar, Laagschardammerweg 3, Schardam; Eduard Theodorus Verveen, Westlandgracht 87''', Amsterdam, all of Netherlands

[21] Appl. No.: 623,075

[22] Filed: Oct. 16, 1975

[30] Foreign Application Priority Data

Oct. 16, 1974 Netherlands .......................... 7413569

[51] Int. Cl.$^2$ ........................ A61B 5/08; A61H 31/00
[52] U.S. Cl. .................... 128/2 R; 128/2 S; 128/DIG. 29
[58] Field of Search ......... 128/2 S, 2 R, 28, DIG. 17, 128/DIG. 29, 1 R; 340/279

[56] References Cited

U.S. PATENT DOCUMENTS

| | | | |
|---|---|---|---|
| 2,934,060 | 4/1960 | Satter | 128/1 R |
| 3,802,417 | 4/1974 | Lang | 128/2 R |
| 3,875,929 | 4/1975 | Grant | 128/2 S |

OTHER PUBLICATIONS

Frank et al., "Treatment of Apnea . . . Arrestor," Pediatrics, vol. 51, No. 5, May, 1973, pp. 878–883.

*Primary Examiner*—Dalton L. Truluck
*Assistant Examiner*—Lee S. Cohen
*Attorney, Agent, or Firm*—Haseltine, Lake & Waters

[57] ABSTRACT

A portable apparatus for regulating the breathing pattern of a patient intended to be used as a remedy against the hyperventilation syndrome. A sensor attached to the body of the patient responds to movements of the chest. The output signals of the sensor are converted into control impulses having a repetition frequency equal to the breathing frequency and providing a criterion for the regulation. The regulation is performed with the aid of a tone generator alternately producing two audible tones having a different character. This tone generator is only in operation if the breathing frequency of the patient is below a prescribed limit frequency.

15 Claims, 3 Drawing Figures

APPARATUS FOR REGULATING THE BREATHING PATTERN

BACKGROUND OF THE INVENTION

The invention relates to an apparatus for regulating the breathing pattern of a patient, comprising a sensor adapted to be attached to the body of the patient and responsive to the contractions and expansions of the chest, and means to convert the output signals of the sensor into short control impulses of which the repetition frequency is equal to the breathing frequency, and which provide a criterion for the regulation of the breathing pattern.

U.S. Pat. No. 3,802,417 (Lang) discloses an apparatus of this kind to regulate the breathing pattern of a premature or newborn child. In this case the control impulses derived from the output signals of the sensor are counted for a predetermined period, for instance ten seconds. If the number of impulses within that period is below a predetermined value, an artificial respiration device is actuated to restore a regular breathing pattern. In the regulation of the breathing pattern of a small child the use of a sensor responsive to the contractions and expansions of the chest may be unsatisfactory, because control impulses may be generated by body movements that have nothing to do with breathing. It is therefore preferred in such a case to use a sensor inserted in the nose or the throat and responsive to the respiration air flow.

U.S. Pat. No. 2,934,060 (Satter) discloses a tone generator alternately producing two audible tones having a different character for the purpose of putting a person to sleep. In this case the repetition frequency of the audible tones is initially adjusted to the breathing frequency of the person. The tone generator is constructed in such manner that the repetition frequency of the tones is gradually reduced, thereby inducing a reduction of the breathing frequency whereby the person eventually goes asleep. It is of course not useful in this case to control the operation of the tone generator by means of a sensor.

BRIEF SUMMARY OF THE INVENTION

It is the object of the invention to provide an apparatus of the above-mentioned kind that may be used as a remedy against the hyperventilation syndrome. For that purpose the apparatus must be carried along by the patient so that it is impossible to use a sensor inserted in the nose or in the throat or to use an artificial respiration device to restore the normal breathing pattern.

Hyperventilation is a condition wherein an excessive quantity of carbon dioxide is removed from the blood by the lungs due to a too rapid or too deep respiration. The carbon dioxide tension and the acidity of the blood are thereby reduced so that it is rendered more difficult for the tissues to take up oxygen from the blood. Thus similar phenomena may occur as in the case of an oxygen deficiency.

The hyperventilation may occur spontaneously, for instance as a consequence of emotions or of heavy physical efforts. Most persons are able to terminate the hyperventilation without difficulty whereby the carbon dioxide contents of the blood return to the normal value.

However, there are persons for whom the termination of the hyperventilation is impossible. The continued hyperventilation gives rise in these persons to very different phenomena which are indicated by the general expression "hyperventilation syndrome". There phenomena may comprise inter alia, a reduction of the consciousness which may be followed by a coma, tetanic spasms of the muscles, tingling feelings or sensations of terror. The hyperventilation syndrome occurs rather frequently in young adults, in particular sportsmen and soldiers.

The invention provides an apparatus by means of which the phenomena may be avoided.

According to the invention the apparatus is constructed in such manner that it may be carried along by a patient as a remedy against the hyperventilation syndrome, and the regulation of the breathing pattern is obtained by means of a tone generator alternately producing two audible tones having a different character which may be perceived by the patient, the control impulses being supplied to the reset terminal of a timing member adapted to deliver an output signal after elapse of a predetermined time interval, in such manner that the timing member only provides output signals if the breathing frequency is below a predetermined limit value, and means being provided to prevent the operation of the tone generator when the output signals of the timing member occur regularly. The tone generator may produce, for instance, a uniform high tone to suggest the inhalation and, a uniform low tone to suggest the exhalation. The patient is instructed to inhale during the occurrence of the high tone, and to exhale during the occurrence of the low tone. After some exercise the patient is conditioned in such manner that his breathing pattern is automatically synchronised with the apparatus. The audible tones may be made perceptible to the patient, for instance, by means of an ear phone so that he is not disturbed by other sounds.

The timing member may be implemented as a counter controlled by a clock generator and, delivering an output signal at a predetermined count. In a preferred embodiment of the invention the output signals of the counter are supplied to a memory condenser which is continuously discharged through a shunt resistor, so that it only carries a substantial voltage if the breathing frequency is below the limit frequency.

The use of this memory condenser has the advantage that the response of the control circuit is adapted to the condition of the patient. If the patient has breathed for some time at a normal frequency, the memory condenser has a relatively high voltage, so that it takes some time before the condenser voltage has been reduced sufficiently to actuate the tone generator. On the other hand if the patient has breathed with a frequency near to the limit frequency so that the counter has missed some of the output signals, the memory condenser only has a low voltage so that the tone generator is rapidly actuated upon a further increase of the breathing frequency. By these means the tone generator is prevented from being actuated by an incidental increase of the breathing frequency.

The voltage across the memory condenser may be used to control a first Schmitt trigger, which is set when the limit frequency is surpassed, and reset when the breathing frequency falls below the limit frequency, and the output voltage of the first Schmitt trigger may be supplied to a second Schmitt trigger so that the same is also set when the limit frequency is surpassed, whereby the feed voltage of the tone generator is switched on. Preferably the second Schmitt trigger actuates, when it is set, a control transistor, whereby the base voltage of a switching transistor inserted in the feed circuit of the tone generator is changed in such manner that the switching transistor is rendered conductive and admits the feed voltage.

In principle the tone generator of the apparatus according to the invention is automatically stopped as soon as the breathing frequency of the patient falls below the limit frequency. However, this involves the danger that the patient relapses into the condition of hyperventilation when the tone generator is stopped. In order to prevent such an incident the tone generator may be kept in operation for some time after the breathing frequency has fallen below the limit frequency. For this purpose the second Schmitt trigger may be kept in its set condition after the first Schmitt trigger has been reset by a holding voltage which is removed after a predetermined time delay. In this case the holding voltage of the second Schmitt trigger may be removed by a delay member which is actuated by a voltage impulse occurring upon the resetting of the first Schmitt trigger. In many cases it will be difficult for a patient being in a condition of hyperventilation to adjust his breathing pattern immediately to the described pattern when the tone generator is switched on. This difficulty may be removed by a construction wherein the tone generator operates immediately after it has been switched on at a relatively high repetition frequency, this frequency being gradually reduced to a predetermined standard value.

If the audible tones are generated by an oscillator controlled by a modulator it is of advantage if the modulator produces a square wave of which the two intervals are adjustable to the desired duration of the inhalation and the exhalation, respectively. In this case the repetition frequency of the square wave may be increased, when the tone generator is switched on, and gradually reduced to a standard value. If the modulator is implemented as a multivibrator, the frequency increase of the square wave may be brought about by an increase of the charging voltage of the condensers of the multivibrator. The frequency increases of the square wave may be initiated by a voltage impulse occurring upon the setting of the first Schmitt trigger.

The said increase of the charging voltage of the condensers of the multivibrator may be obtained in such manner that the charging voltage is produced by a voltage divider, connected to the feed voltage and consisting of two resistors, one of the resistors being shunted by a short-circuiting transistor, and that the voltage impulse occurring upon the setting of the first Schmitt trigger charges a control condenser which is continuously discharged through a shunt resistor, the voltage across the control condenser being used to control the short-circuiting resistor.

Since the tone generator is automatically switched on, it is generally not possible to adjust the character of the audible tones to the needs of the patient. It is therefore desirable to choose the character of the tones in such manner that they are suitable to suggest the desired breathing pattern in all circumstances. For this purpose it is preferable that one of the tones generated by the tone generator has a progressively increasing frequency and the other tone has a progressively decreasing frequency. This makes it possible for the patient to anticipate the termination of each tone whereby the adaptation to the required pattern is easier; this may be realised by supplying the square wave produced by the modulator to a modulating condenser so that the same is alternately charged, and discharged and by using the voltage across the modulating condenser to determine the frequency of the generated tones. If the oscillator is implemented as a multivibrator, the voltage across the modulating condenser may determine the charging voltage of the condensers of the multivibrator.

DETAILED DESCRIPTION

Figure 1:
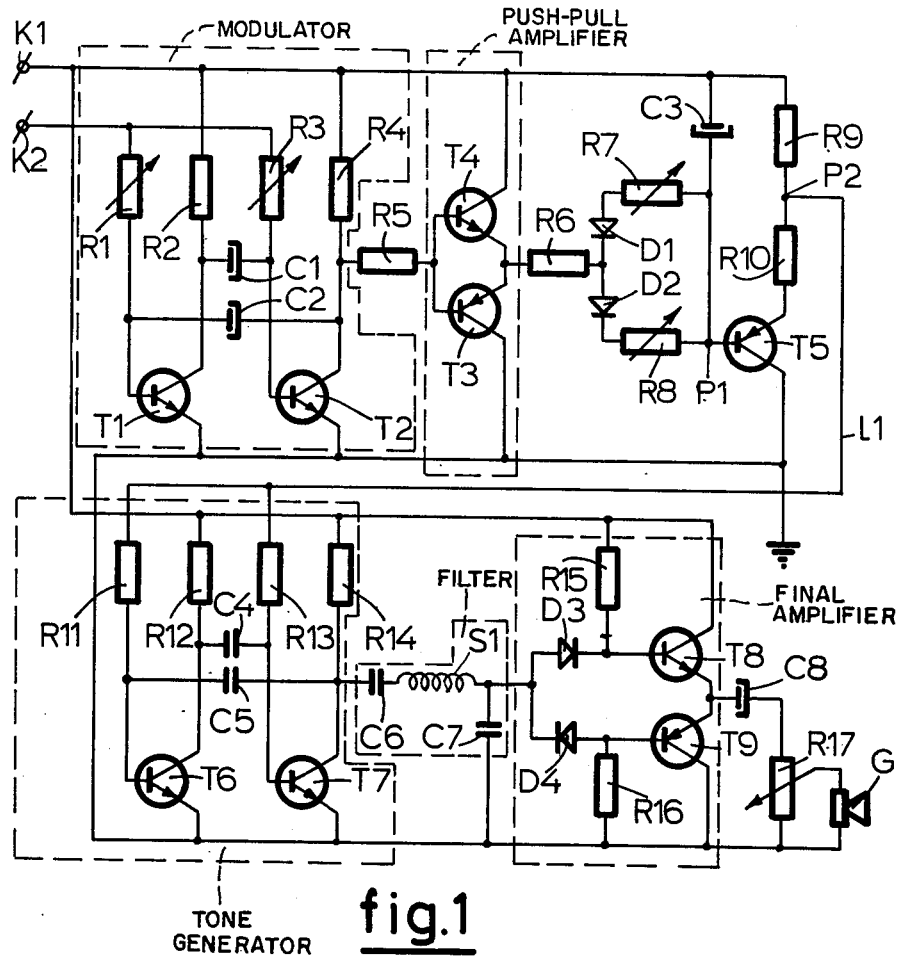
FIG. 1 shows the circuit diagram of a tone generator of an apparatus according to the invention.

The tone generator shown in FIG. 1 comprises a modulator implemented as a multivibrator and provided with two transistors T1 and T2 of which the collectors are cross-wise connected with the base electrodes through condensers C1 and C2. Furthermore, the multivibrator contains four resistors R1 – R4, of which the resistors R1 and R3 are adjustable. The resistors R2 and R4 are connected with a terminal K1 carrying the full battery voltage whereas the resistors R1 and R3 are connected with a terminal K2 of which the voltage is variable.

If transistor T1 is rendered conductive at a certain moment, the left terminal of condenser C1 is grounded, so that this condenser is charged through resistor R3. As soon as the voltage across condenser C1 has reached a predetermined threshold value, transistor T2 is rendered conductive, and a voltage impulse is transmitted to the base of transistor T1 through condenser C2, whereby transistor T1 is cut off. After that, condenser C2 is charged through resistor R1. It will be clear that the durations of the two conditions of the multivibrator may be separately adjusted by means of the resistors R1 and R3. Furthermore, the charging of condensers C1 and C2 may be accelerated by increasing the voltage on terminal K2, whereby the repetition frequency of the multivibrator is increased.

The modulator, consisting of transistors T1 and T2, condensers C1 and C2, and resistors R1 – R4 produces a square wave voltage of which the two intervals may be adjusted to the desired durations of the inhalation and the exhalation, respectively. This square wave voltage is supplied through a resistor R5 to the base electrodes of a pair of transistors T3 and T4 of opposite conductivity type. The interconnected emitters of these transistors are connected through a resistor R6 with two diodes D1 and D2 passing current in opposite directions; these diodes are connected through adjustable resistors R7 and R8 with a condenser C3.

If a negative voltage is supplied through resistor R5 to the base electrodes of transistor T3 and T4 at a certain moment, transistor T3 is rendered conductive, so that condenser C3 is grounded through resistor R7, diode D1, resistor R6 and transistor T3. Condenser C3 is thereby charged, so that the voltage of point P1 is reduced.

If a positive voltage is supplied through resistor R5 to transistors T3 and T4, transistor T4 is rendered conductive, so that condenser C3 is discharged through resistor R8, diode D2, and resistor R6. As a consequence, the voltage of point P1 is increased.

Point P1 is connected with the base of a transistor T5 of which the collector circuit contains two series connected resistors R9 and R10. During the interval in which the voltage of point P1 is progressively reduced by the charging of condenser C3, the emitter current of transistor T5 is gradually increased, whereby the voltage in the connecting point P2 of resistors R9 and R10 decreases. During the interval in which condenser C3 is discharged, the conductivity of transistor T5 is gradually decreased, so that the voltage in point P2 increases. Thus, the line L1, which is connected with point P2, carries a voltage which is alternately progressively increased and progressively decreased in the rhythm of the square wave generated by the modulator. This voltage is used for a frequency modulation of the oscillator, which is implemented as a multivibrator, and is provided with two transistors T6 and T7, two condensers C4 and C5, and four resistors R11 – R14. This oscillator produces an audible tone having an average frequency of about 200 cps. The charging voltage of the condensers C4 and C5 is provided by line L1. During the interval in which the voltage on line L1 is progressively increased, the frequency of the oscillator is likewise increased to a value of about 250 cps. During the interval in which the voltage on line L1 is progressively decreased, the frequency of the oscillator is reduced to about 160 cps. Thus, two tones are alternately generated by the oscillator, in such manner that the frequency of one of these tones increases progressively, and the frequency of the other tone decreases progressively. The said oscillator frequencies are determined, inter alia, by the capacity of the modulating condenser C3.

The tones produced by the oscillator are supplied through a low-pass filter, comprising two condensers C6 and C7 and an inductance S1, to a final amplifier, comprising two diodes D3 and D4, two resistors R15 and R16 and two transistors T8 and T9 of opposite conductivity type. The transistors operate, in combination, as a push-pull amplifier. The output signal is supplied through a condenser C8 to a potentiometer R17, connected with a sound reproducer G, such as a loudspeaker or an ear telephone. The potentiometer R17 serves as a volume control.

Figure 2:
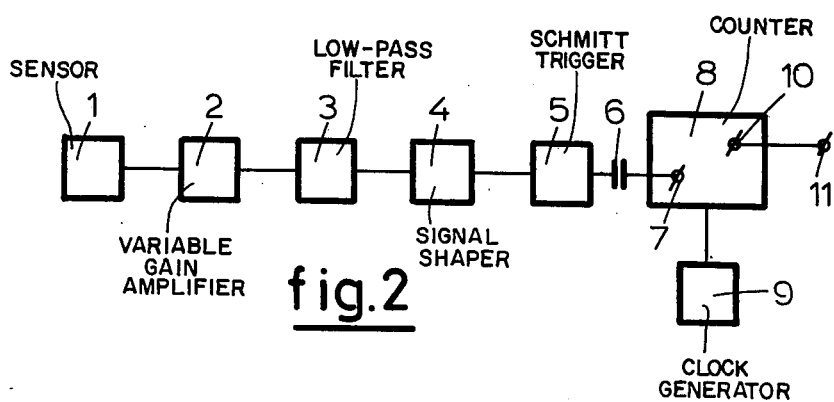
FIG. 2 shows a block diagram of a circuit for determining the breathing frequency of the patient and for comparing the same with a described limit frequency.

The circuit shown in FIG. 2 comprises a sensor 1 attached to the body of the patient and serving to observe the breathing pattern of the patient. The sensor may be implemented in various manners. It is possible, for instance, to use a microphone, but it is generally preferred to use a variable resistor such as a strain gauge or a mercury wire sensor. The mercury wire sensor consists of a flexible tube made of silicon rubber, and having, for instance, a diameter of 0.5 mm, which is filled with mercury and provided with wire-shaped electrodes at its ends. If this sensor is attached to the chest of a patient, the tube is alternately expanded and contracted in the rhythm of the breathing. Preferably, the mercury wire sensor is combined with three fixed resistors into a Wheatstone bridge. The output signal of the bridge is supplied to a variable gain amplifier 2, after which the amplified signal is led to a low-pass filter 3 to eliminate all interferences having frequencies of more than 1 cps. The signal now passes a signal shaper 4, delivering a pure square wave. This square wave is supplied to a Schmitt trigger 5, which is alternately brought into each of its stable conditions in the rhythm of the breathing of the patient. The output voltage of the trigger in one of those conditions is applied through a condenser 6 to the reset terminal of a counter 8 controlled by a clock generator 9. The terminal 7 receives sharp impulses of which the repetition frequency is equal to the breathing frequency of the patient. The counter is provided with an output terminal 10, through which a signal is delivered each time when a predetermined position of the counter is reached; this signal is supplied to a connecting terminal 11.

If the patient has a normal breathing pattern, the interval between successive impulses supplied to terminal 7 is so long that the counter reaches the position in which the output signal is delivered during each breathing cycle. In this case, periodic impulses appear on terminal 11.

If the patient gets into a condition of hyperventilation, the interval between successive impulses supplied to terminal 7 becomes so short that the counter is reset each time before it can reach the position in which the output signal is delivered. In this case, no impulses appear on terminal 11.

Figure 3:
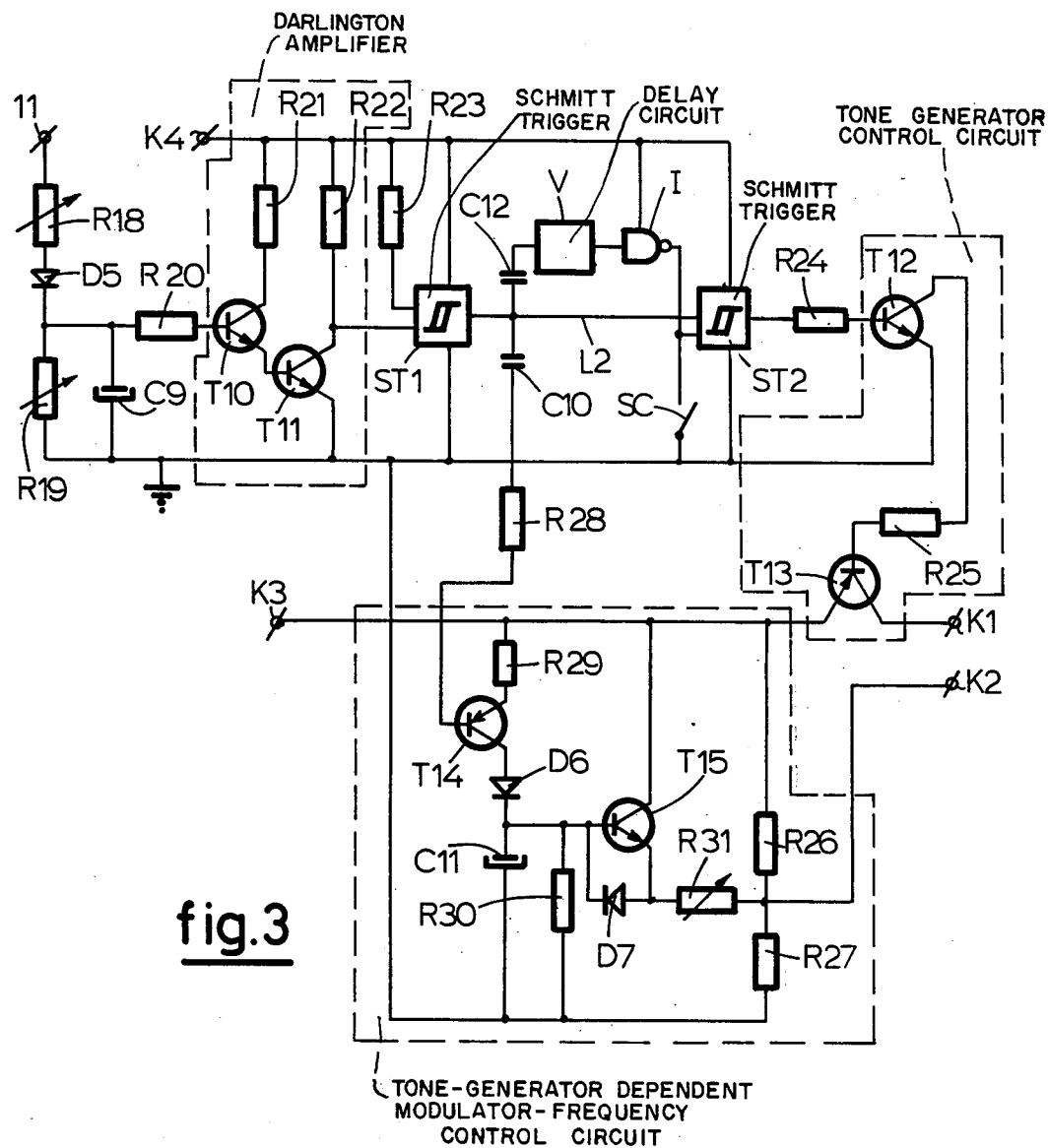
FIG. 3 shows the circuit for controlling the operation of the tone generator in dependence of the output signals of the circuit according to FIG. 2.

In the control circuit shown in FIG. 3, the periodic impulses appearing on terminal 11 (FIG. 2) when the breathing frequency is below the prescribed limit frequency are supplied through an adjustable resistor 18 in series with a diode D5 to a memory condenser C9, provided with an adjustable shunt resistor R19. The resistors R18 and R19 determine the time constants of the charging and discharging of the memory condenser C9, respectively.

If the breathing frequency is below the limit frequency, condenser C9 has a positive voltage which is supplied through a resistor R20 to the input terminal of a Darlington amplifier, comprising two transistors T10 and T11, and two resistors R21 and R22. The collector of transistor T11 is connected with one of the input terminals of a Schmitt trigger ST1, of which the other input terminal is connected through a resistor R23 with the positive pole of the feed source.

If condenser C9 has a positive voltage, indicating that the breathing frequency is normal, transistors T10 and T11 are conductive, so that the input terminal of the Schmitt trigger ST1 connected with transistor T11 is at ground potential. Under these circumstances, a positive voltage occurs in the output line L2 of the trigger; this voltage is supplied to one of the input terminals of a second Schmitt trigger ST2, which delivers, under these circumstances, a negative voltage, transmitted through a resistor R24 to the base of a control transistor T12.

As soon as the patient gets into a condition of hyperventilation, no impulses are supplied to terminal 11 anymore, so that memory condenser C9 is discharged. As soon as the voltage across the memory condenser falls below a predetermined value, transistors T11 and T12 are cut off, so that the collector of transistor T11 is supplied with a high voltage. Schmitt trigger ST1 is set thereby, so that a negative voltage occurs in the output line L2. This voltage causes Schmitt trigger ST2 to be set, whereby a positive voltage is supplied to the base of control transistor T12. The collector of transistor T12 is connected through a resistor R25 with the base of a switching transistor T13 adapted to transmit the battery voltage on terminal K3 to the feed terminal K1 of the tone generator (FIG. 1).

As long as the patient has a normal breathing pattern, the control transistor T12 is cut off, whereby switching transistor T13 is likewise cut off. The tone generator is then out of operation. If the patient gets into a condition of hyperventilation, control transistor T12 is rendered conductive whereby the base of switching transistor T13 is approximately grounded and transistor T13 is rendered conductive. The tone generator is thereby switched on.

The charging voltage of condensers C1 and C2 of the modulator (FIG. 1), occurring on terminal K2, is taken from a voltage divider consisting of the resistors R26 and R27 and connected between the positive pole K3 of the battery and ground. As a consequence, the charging voltage of the modulator condensers is equal to about half the battery voltage under normal circumstances. However, the charging voltage is increased immediately after the tone generator has been switched on. For this purpose, the output line L2 of trigger ST1 is connected through a condenser C10 and a resistor R28 with the base of a transistor T14. If line L2 obtains a negative voltage due to the setting of trigger ST1, a negative voltage impulse is supplied to the base of transistor T14, whereby this transistor is rendered conductive for a short time, and a condenser C11 is suddenly charged through a resistor R29 and a diode D6. A resistor R30 is connected in parallel with condenser C11. The voltage across condenser C11 is supplied to the base of a transistor T15 which is thereby rendered conductive, so that resistor R26 of the voltage divider is short-circuited through an adjustable resistor R31. The full battery voltage is thereby applied to terminal K2. Condenser C11 is now discharged through resistor R30, so that transistor T15 is gradually cut off. Thus, the voltage of terminal K2 is gradually reduced to its normal value.

As a consequence, the repetition frequency of the square wave produced by the modulator is increased when the tone generator is switched on, and gradually reduced to its normal value, the rate of this reduction being determined by the time constant of the combination of condenser C11 and resistor R30. A diode D7 conducting in opposite sense is arranged in parallel with the base-emitter-path of transistor T15.

As soon as the breathing frequency of the patient has returned to an acceptable value, impulses reappear at terminal 11, so that the memory condenser C9 is recharged. Transistors T10 and T11 are thereby rendered conductive, so that trigger ST1 is reset and a positive voltage reappears in line L2. However, trigger ST2 is not yet reset, because a positive holding voltage is supplied through an inverter I to the second input terminal of this trigger. Line L2 is connected through a condenser C12 with a delay circuit V, of which the output terminal is connected with the inverter I. Thus, a positive voltage impulse is supplied to the delay circuit V when trigger ST1 is reset; this impulse reaches the inverter after elapse of the delay time which may amount, for instance, to two minutes, so that the inverter supplies a negative impulse to the second input terminal of trigger ST2. Trigger ST2 is now also reset, so that transistor T13 is cut off and the tone generator is put out of operation. Thus, the tone generator remains operative during some minutes after the breathing frequency of the patient has returned to its normal value, so that a relapse into the condition of hyperventilation is prevented.

By means of a switch SC, the second input terminal of trigger ST2 may be grounded at any time to switch off the tone generator. The control circuit is fed through terminal K4 with a stabilized direct voltage derived from the battery by means of a Zener diode and a series connected resistor.

We claim:

1. Portable apparatus for regulating the breathing pattern of patient, in particular as a remedy against the hyperventilation syndrome, comprising a sensor adapted to be attached to the body of the patient, said sensor including means responsive to the contractions and expansions of the chest for producing sensor output signals, means connected to said sensor for converting the output signals of said sensor into short control impulses of which the repetition frequency is equal to the breathing frequency, timing means adapted to deliver an output signal after elapse of a predetermined time interval and having a reset terminal, means connecting said signal converting means to said reset terminal for supplying said control impulses to said reset terminal so that said timing means only provides output signals if the breathing frequency is below a prescribed limit frequency, tone generator means connected to said timing means for alternately producing two audible tones having a different character, means for rendering said tones perceptible to the patient connected to said tone generator means, and means connected to said timing means for preventing the operation of said tone generator means connected to said timing means when the ouput signals of said timing means occur regularly.

2. Apparatus as claimed in claim 1, wherein said timing means includes a counter resetable by said control impulses supplied to said reset terminal, means for delivering an output signal from said counter at a predetermined count, and further comprising a clock generator, said clock generator including means for controlling said counter.

3. Apparatus as claimed in claim 2, wherein said tone generator preventing means further comprises a memory condenser, a shunt resistor in parallel with said memory condenser so as to discharge the same continuously, and means for supplying the output signals of said counter to said memory condenser, the latter means being connected to said memory condenser and said shunt resistor, so that said memory condenser only carries a substantial voltage if the breathing frequency is below said limit frequency.

4. Apparatus as claimed in claim 3, wherein said tone generator preventing means further comprises a first Schmitt trigger, means connecting said memory condenser with said Schmitt trigger for controlling said first Schmitt trigger in dependence on the voltage across said memory condenser, so that said first Schmitt trigger is set when said limit frequency is surpassed and reset when the breathing frequency falls below said limit frequency, a second Schmitt trigger connected to said first Schmitt trigger and controlled by the output voltage of said first Schmitt trigger in its set condition, so that said second Schmitt trigger is also set when said limit frequency is surpassed, and means connected to and controlled by said second Schmitt trigger in its set condition for switching on said tone generator means.

5. Apparatus as claimed in claim 4, wherein said means for switching on said tone generator means comprise a control transistor actuated by said second Schmitt trigger, and a switching transistor in the feed circuit of said tone generator means connected to and controlled by said control transistor.

6. Apparatus as claimed in claim 1, wherein said tone generator preventing means further comprises means for keeping said tone generator means in operation for some time after the breathing frequency has fallen below said limit frequency.

7. Apparatus as claimed in claim 4, wherein said tone generator preventing means further comprises means for supplying a holding voltage to said second Schmitt trigger to keep the same in its set condition after said first Schmitt trigger has been reset, and means for interrupting said holding voltage after a predetermined time delay.

8. Apparatus as claimed in claim 7, wherein said means for interrupting said holding voltage comprise a delay member actuated by a voltage impulse occurring upon the resetting of said first Schmitt trigger, said delay member being connected to said first Schmitt trigger.

9. Apparatus as claimed in claim 1, wherein said tone generator means comprises oscillator means generating said audible tones, modulator means connected to and controlling said oscillator means and producing a square wave, said modulator means including means for adjusting the durations of the two intervals of said square wave, and means connected to said modulator means for increasing the repetition frequency of said square wave when the tone generator means is switched on, and for gradually reducing said repetition frequency to a standard value.

10. Apparatus as claimed in claim 9, wherein said modulator means is implemented as a multivibrator, said multivibrator including two transistors and two condensers each connecting the collector of one of said transistors with the base of the other of said transistors, and further comprising means connected to said modulator means for temporarily increasing the charging voltage of said condensers when said tone generator means is switched on.

11. Apparatus as claimed in claim 10, further comprising a first Schmitt trigger included in said tone generator preventing means and arranged so that is is set when said limit frequency is surpassed and reset when the breathing frequency falls below said limit frequency, output terminals of said first Schmitt trigger being connected with said means for increasing the charging voltage of the condensers of said multivibrator, the latter means being actuable by a voltage impulse occurring at output terminals of said first Schmitt trigger when the same is set.

12. Apparatus as claimed in claim 11, wherein the means for increasing the charging voltage of said condensers comprise a voltage divider, the latter including two series connected resistors, a short-circuiting transistor in parallel with one of said resistors, a control condenser connected to said short-circuiting transistor, means connected with the output terminals of said first Schmitt trigger for controlling the charging of said control condenser, so that said control condenser is charged upon the occurrence of said voltage impulse, a shunt resistor in parallel with said control condenser to discharge the same continuously, means for controlling said short-circuiting transistor in dependence on the voltage across said control condenser, and means for supplying the output voltage of said voltage divider as a charging voltage to the condensers of said multivibrator.

13. Apparatus as claimed in claim 9, further including means connected to said modulator means for frequency modulating the tone generator means produced audible tones for one of the tones to progressively increase in frequency during one of said two intervals of said square wave, and for the other of said tones to progressively decrease in frequency during the other of said intervals.

14. Apparatus as claimed in claim 13, wherein the frequency-modulating means further comprise a modulating condenser, means connected to said modulator means for supplying said square wave to said modulating condenser for the latter to be alternately charged and discharged, and means connected to said oscillator means for supplying the voltage across said modulating condenser to said oscillator means, to determine the frequency of the generated tones.

15. Apparatus as claimed in claim 14, wherein said oscillator means is implemented as a multivibrator, said oscillator means including two transistors and two condensers, each connecting the collector of one of the said transistors with the base of the other one, and further comprising means to supply the voltage across said modulating condenser as a charging voltage to the condensers of said multivibrator.

* * * * *